(12) United States Patent
Federspiel et al.

(10) Patent No.: US 7,829,759 B2
(45) Date of Patent: *Nov. 9, 2010

(54) GENERATION OF PLANTS WITH IMPROVED PATHOGEN RESISTANCE

(75) Inventors: Nancy Anne Federspiel, Menlo Park, CA (US); Allan Lammers, Portland, OR (US); Xing Liang Liu, Tualatin, OR (US); Stanley R. Bates, Vail, AZ (US); Christina Westerlund, Portland, OR (US); Jonathan R. Fitch, Portland, OR (US)

(73) Assignee: Agrinomics LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/400,577

(22) Filed: Mar. 9, 2009

(65) Prior Publication Data
US 2009/0193540 A1 Jul. 30, 2009

Related U.S. Application Data

(63) Continuation of application No. 10/512,600, filed as application No. PCT/US2003/012981 on Apr. 24, 2003, now Pat. No. 7,521,592.

(60) Provisional application No. 60/375,333, filed on Apr. 24, 2002.

(51) Int. Cl.
*A01H 5/00* (2006.01)
*C12N 15/09* (2006.01)
*C12N 15/82* (2006.01)

(52) U.S. Cl. .................. 800/279; 800/278; 800/298; 435/468; 435/430.1

(58) Field of Classification Search ................. None
See application file for complete search history.

(56) References Cited

U.S. PATENT DOCUMENTS

| | | | |
|---|---|---|---|
| 5,856,154 A | 1/1999 | Ryals et al. | |
| 5,939,601 A | 8/1999 | Klessig et al. | |
| 6,031,153 A | 2/2000 | Ryals et al. | |
| 6,057,490 A | 5/2000 | Ryals et al. | |
| 6,664,446 B2 | 12/2003 | Heard et al. | |
| 7,135,616 B2 | 11/2006 | Heard et al. | |
| 7,521,592 B2 * | 4/2009 | Federspiel et al. | .......... 800/279 |
| 2002/0160378 A1 | 10/2002 | Harper et al. | |
| 2003/0226173 A1 | 12/2003 | Ratcliffe et al. | |
| 2004/0019927 A1 | 1/2004 | Sherman et al. | |
| 2004/0237137 A1 | 11/2004 | Osumi et al. | |

FOREIGN PATENT DOCUMENTS

| | | |
|---|---|---|
| WO | WO 96/31608 | 9/1996 |
| WO | WO 02/16655 | 2/2002 |
| WO | WO 03/013227 | 2/2003 |

OTHER PUBLICATIONS

Aarts et al., "Different requirements for *EDS1* and *NDR1* by disease resistance genes define at least two R gene-mediated signaling pathways in *Arabidopsis*," *Proc Natl. Acad. Sci.* USA, 95:10306-10311, 1998.
Asai et al., "MAP kinase signaling cascade in *Arabidopsis* innate immunity," *Nature*, 415:977-983, 2002.
Bennetzen and Jones, "Approaches and Progress in the Molecular Cloning of Plant Disease Resistance Genes," Genetic Engineering, 14:99-124, 1992.
Berrocal-Lobo et al., "Constitutive expression of Ethylene-Response-Factor1 in *Arabidopsis* confers resistance to several necrotrophic fungi," *The Plant Journal*, 29(1):23-32, 2002.
Bowling et al., "A mutation in arabidopsis that leads to constitutive expression of systemic acquired resistance," *Plant Cell*, 6:1845-1857, 1994.
Bowling et al., "The *cpr5* mutant of arabidopsis expresses both NPR1-dependent and NPR1-independent resistance," *Plant Cell*, 9:1573-1584, 1997.
Cao et al., "Effect of two conserved amino acid residues on DREB1A function," *Biochemistry (Mosc).*, 66(6):623-627, 2001.
Cao et al., "Generation of broad-spectrum disease resistance by overexpression of an essential regulatory gene in systemic acquired resistance," *Proc. Natl. Acad. Sci.* USA, 95:6531-6536, 1998.
Chen et al., "Expression profile matrix of *Arabidopsis* transcription factor genes suggests their putative functions in response to environmental stresses," *The Plant Cell*, 14(3):559-574, 2002.
Clarke et al., "Constitutive disease resistance requires *EDS1* in the *Arabidopsis* mutants *cpr1* and *cpr6* and is partially *EDS1*-dependent in *cpr5*," *The Plant Journal*, 26:409-420, 2001.
Clarke et al., "Roles of salicylic acid, jasmonic acid, and ethylene in *cpr*-induced resistance in *Arabidopsis*," *The Plant Cell*, 12:2175-2190, 2000.
Clarke et al., "Uncoupling PR gene expression from NPR1 and bacterial resistance: characterization of the dominant Arabidopsis *cpr6-1* mutant," *The Plant Cell*, 10:557-569, 1998.
Dangl and Jones, "Plant pathogens and integrated defense responses to infection," *Nature*, 411:826-833, 2001.
Delaney et al., "*Arabidopsis* signal transduction mutant defective in chemically and biologically induced disease resistance," *Proc. Natl. Acad. Sci.* USA, 92:6602-6606, 1995.
Devadas et al., "The *Arabidopsis hrl1* mutation reveals novel overlapping roles for salicylic acid, jasmonic acid and ethylene signalling in cell death and defence against pathogens," *The Plant Journal*, 30(4):467-480, 2002.
Dewdney et al., "Three unique mutants of *Arabidopsis* identify *eds* loci required for limiting growth of a biotrophic fungal pathogen," *The Plant Journal*, 24(2):205-218, 2000.
Feys and Parker, "Interplay of signaling pathways in plant disease resistance," *TIG*, 16(10):449-455, 2000.
Frye and Innes, "An *Arabidopsis* mutant with enhanced resistance to powdery mildew," *The Plant Cell*, 10:947-956, 1998.
GenBank Accession No. AAM63284, Jan. 27, 2006.
GenBank Accession No. AAN32899, Dec. 21, 2004.

(Continued)

*Primary Examiner*—Medina A Ibrahim
(74) *Attorney, Agent, or Firm*—Klarquist Sparkman, LLP

(57) ABSTRACT

The present invention is directed to plants that display a pathogen resistance phenotype due to altered expression of a PPR2 nucleic acid. The invention is further directed to methods of generating plants with a pathogen resistance phenotype.

5 Claims, No Drawings

OTHER PUBLICATIONS

GenBank Accession No. AAN77067, Dec. 2, 2002.
GenBank Accession No. ABX57121, Feb. 20, 2003.
GenBank Accession No. ADD30328, Jan. 15, 2004.
GenBank Accession No. ADI44257, Apr. 22, 2004.
GenBank Accession No. B84718, Feb. 2, 2001.
GenBank Accession No. BAC21532, Oct. 17, 2002.
GenBank Accession No. BAC21534, Feb. 16, 2008.
GenBank Accession No. NP_180681, Aug. 20, 2002.
GenBank Accession No. NP_188965, May 22, 2008.
Geneseq Database accession No. AAG30582, Oct. 17, 2000.
Glazebrook, Jane, "Genes controlling expression of defense responses in *Arabidopsis*," *Current Opinion in Plant Biology*, 2:280-286,1999.
Glazebrook, Jane, "Genes controlling expressions of defense responses in *Arabidopsis*—2001 status," *Current Opinion in Plant Biology*, 4:301-308, 2001.
Gu et al., "Tomato transcription factors Pti4, Pti5, and Pti6 activate defense responses when expressed in *Arabidopsis*," *The Plant Cell*, 14:817-831, 2002.
Hailing Jin et al., Plant Molecular Biology, 41:577-585 1999.
Heath. Michéle C., "Nonhost resistance and nonspecific plant defenses," *Current Opinion in Plant Biology*, 3:315-319, 2000.
Kachroo et al., "A fatty acid desaturase modulates the activation of defense signaling pathways in plants," *PNAS*, 98:9448-9453, 2001.
Kim and Delaney, "*Arabidopsis* SON1 is an F-box protein that regulates a novel induced defense response independent of both salicylic acid and systemic acquired resistance," *The Plant Cell*, 14:1469-1482, 2002.
Kim and Delaney, "Over-expression of *TGA5*, which encodes a bZIP transcription factor that interacts with NIM1/NPR1, confers SAR-independent resistance in *Arabidopsis thaliana* to *Peronospora parasitica*," *Plant J.*, 32:151-163, 2002.
Kinkema et al., "Nuclear localization of NPR1 is required for activation of *PR* gene expression," *The Plant Cell*, 12:2339-2350, 2000.
Lin et al., "*Arabidopsis thaliana* chromosome 1 BAC F22H5 genomic sequence, complete sequence," Genbank accession No. AC025814, 2001, (retrieved Jan. 14, 2005).
Lorenzo et al., "Ethylene Response Factor1 integrates signals from ethylene and jasmonate pathways in plant defense," *The Plant Cell*, 15(1):165-178, 2003.
Lucht et al., "Pathogen stress increases somatic recombination frequency in *Arabidopsis*," *Nature Genetics*, 30:311-314, 2002.
Mach et al., "The *Arabidopsis*-accelerated cell death gene *ACD2* encodes red chlorophyll catabolite reductase and suppresses the spread of disease symptoms," *Proc. Natl. Acad. Sci.* USA, 98(2):771-776, 2001.
Maldonado et al., "A putative lipid transfer protein involved in systemic resistance signaling in *Arabidopsis*," *Nature*, 419:399-403, 2002.
Maleck et al., "Isolation and characterization of broad-spectrum disease-resistant *Arabidopsis* mutants," *Genetics*, 160:1661-1671, 2002.
McDowell et al., "Downy mildew (*Peronospora parasitica*) resistance genes in *Arabidopsis* vary in functional requirements for *NDR1*, *EDS1*, *NPR1* and salicylic acid accumulation," *Plant J.*, 22:523-529, 2000.
Molina et al., "Inhibition of protoporphyrinogen oxidase expression in *Arabidopsis* causes a lesion-mimic phenotype that induces systemic acquired resistance," *The Plant Journal*, 17(6):667-678, 1999.
Morel and Dangl, "Suppressors of the *Arabidopsis lsd5* cell death mutation identify genes involved in regulating disease resistance repsonses," *Genetics*, 151:305-319, 1999.
Nürnberger and Scheel, "Signal transmission in the plant immune response," *TRENDS in Plant Science*, 6(8):372-379, 2001.
Onate-Sanchez and Singh, "Identification of *Arabidopsis* ethylene-responsive element binding factors with distinct induction kinetics after pathogen infection," *Plant Physiology*, 128(4):1313-1322, 2002.
Petersen et al., "*Arabidopsis* MAP kinase 4 negatively regulates systemic acquired resistance," *Cell*, 103:1111-1120, 2000.
Reymond and Farmer, "Jasmonate and salicylate as global signals for defense gene expression," *Current Opinion in Plant Biology*, 1:404-411, 1998.
Romeis, Tina., "Protein kinases in the plant defence response," *Current Opinion in Plant Biology*, 4:407-411, 2001.
Rushton et al., "Synthetic plant promoters containing defined regulatory elements provide novel insights into pathogen-and would-inducing signaling," *Plant Cell*, 14:749-762, 2002.
Rustérucci et al., "The disease resistance signaling components *EDS1*and *PAD4* are essential regulators of the cell death pathway controlled by *LSD1* in *Arabidopsis*," *The Plant Cell*, 13:2211-2224, 2001.
Schulze-Lefert and Vogel, "Closing the ranks to attack by powdery mildew," *Trends in Plant Science Reviews*, 5(8):343-348, 2000.
Shah et al., "A recessive mutation in the *Arabidopsis SSI2* gene confers SA- and *NPR1*-independent expression of *PR*genes and resistance against bacterial and oomycete pathogens," *The Plant Journal*, 25(5):563-574, 2001.
Solano et al., "Nuclear events in ethylene signaling: a transcriptional cascade mediated by Ethylene-Insensitive3 and Ethylene-Response-Factor1," *Genes and Development*, 12:3703-3714, 1998.
Stone et al., "Simulation of fungal-mediated cell death by fumonisin B1 and selection of fumonisin B1-resistant (*fbr*) *Arabidopsis* mutants," *The Plant Cell*, 12:1811-1822, 2000.
Stracke et al., Current Opinion in Plant Biology, 4:447-456 2001.
Takemoto et al., "GFP-tagging of cell components reveals the dynamics of subcellular re-organization in response to infection of *Arabidopsis* by oomycete pathogens," *Plant J.*, 33:775-792, 2003.
Tang and Innes, "Overexpression of a kinase-deficient form of the *EDR1* gene enhances powdery mildew resistance and ethylene-induced senescence in *Arabidopsis*," *The Plant Journal*, 32:975-983, 2002.
Tierens et al., "*Esa1*, an *Arabidopsis* mutant with enhanced susceptibility to a range of necrotrophic fungal pathogens, shows a distorted induction of defense responses by reactive oxygen generating compounds," *The Plant Journal*, 29(2):131-140, 2002.
Tör et al., "*Arabidopsis* SGT1b is required for defense signaling conferred by several downy mildew resistance genes," *Plant Cell*, 14:993-1003, 2002.
Tornero and Dangl, "A high-throughput method for quantifying growth of phytopathogenic bacteria *Arabidopsis thaliana*," *The Plant Journal*, 28(4):475-481, 2001.
Vogel and Somerville, "Isolation and characterization of powdery mildew-resistant *Arabidopsis* mutants," *Proc. Natl. Acad. Sci.* USA, 97(4):1897-1902, 2000.
Weigel et al., "Activation tagging in *Arabidopsis*," *Plant Physiology*, 122(4):1003-1013, 2000.
Weymann et al., "Suppression and restoration of lesion formation in *Arabidopsis lsd* mutants," *Plant Cell*, 7:2013-2022, 1995.
Xie et al., "COI1: An *Arabidopsis* gene required for Jasmonate-regulated defense and fertility," *Science*, 280:1091-1094, 1998.
Xu et al., "The SCF$^{COI1}$ ubiquitin-ligase complexes are required for jasmonate response in *Arabidopsis*," *The Plant Cell*, 14:1919-1935, 2002.
Yang et al., "Activation of a mitogen-activated protein kinase pathway is involved in disease resistance in tobacco," *Proc Natl Acad Sci* USA, 98(2):741-746, 2001.
Yoshioka et al., "Environmentally sensitive, SA-dependent defense responses in the *cpr22* mutant of *Arabidopsis*," *The Plant Journal*, 26(4):447-459, 2001.
Zhang et al., "Interaction of NPR1 with basic leucine zipper protein transcription factors that bind sequences required for salicylic acid induction of the *PR-1* gene," *Proc Natl Acad Sci* USA, 96:6523-6528, 1999.
Zimmerli et al., "Potentiation pathogen-specific defense mechanisms in *Arabidopsis* by β-aminobutyric acid," *Proc Natl Acad Sci* USA, 97:12920-12925, 2000.

* cited by examiner

GENERATION OF PLANTS WITH IMPROVED PATHOGEN RESISTANCE

The present application is a continuation of U.S. patent application Ser. No. 10/512,600, filed May 9, 2005 now U.S. Pat. No. 7,521,592, which is the U.S. National Stage of International Application No. PCT/US2003/12981, filed Apr. 24, 2003, which was published in English under PCT Article 21(2), which in turn claims the benefit of U.S. Provisional Application No. 60/375,333, filed Apr. 24, 2002, all of which are incorporated herein in their entirety.

BACKGROUND OF THE INVENTION

The control of infection by plant pathogens, which can inhibit production of fruits, seeds, foliage and flowers and cause reductions in the quality and quantity of the harvested crops, is of significant economic importance. Pathogens annually cause billions of dollars in damage to crops worldwide (Baker et al. 1997, Science 276:726-733). Consequently, an increasing amount of research has been dedicated to developing novel methods for controlling plant diseases. Such studies have centered on the plant's innate ability to resist pathogen invasion in an effort to buttress the plant's own defenses to counter pathogen attacks (Staskawicz et al. 1995, Science 268:661-667; Baker et al. supra).

Although most crops are treated with agricultural anti-fungal, anti-bacterial agents and/or pesticidal agents, damage from pathogenic infection still results in revenue losses to the agricultural industry on a regular basis. Furthermore, many of the agents used to control such infection or infestation cause adverse side effects to the plant and/or to the environment. Plants with enhanced resistance to infection by pathogens would decrease or eliminate the need for application of chemical anti-fungal, anti-bacterial and/or pesticidal agents.

There has been significant interest in developing transgenic plants that show increased resistance to a broad range of pathogens (Stuiver and Custers, 2001, Nature 411:865-8; Melchers and Stuiver, 2000, Curr Opin Plant Biol 3:147-52; Rommens and Kishore, 2000, Curr Opin Biotechnol 11:120-5; Mourgues et al. 1998, Trends Biotechnol 16:203-10). The interaction between *Arabidopsis* and the oomycete *Peronospora parasitica* (downy mildew) provides an attractive model system to identify molecular components of the host that are required for recognition of the fungal parasite (Parker et al. 1996 Plant Cell 8:2033-46). A number of genes whose mis-expression is associated with altered resistance to *P. parasitica*, as well as other pathogens, have been identified in *Arabidopsis*. Overexpression of the NPR1 gene confers resistance to infection by *P. parasitica* as well as the bacterial pathogen *Pseudomonas syringae* (Cao et al, 1998 Proc Natl Acad Sci USA 95:6531-6536). CPR6 is semi-dominant mutation implicated in multiple defense pathways (Clarke et al. 1998, Plant Cell 10:557-569). Lsd6 and Lsd7 are dominant mutations that confer heightened disease and result in the development of spontaneous necrotic lesions and elevated levels of salicylic acid (Weymann et al 1995 Plant Cell 7:2013-2022). A number of recessive mutations confer *P. parasitica* resistance, including ssi2, in the SSI2 gene encoding a stearoyl-ACP desaturase (Kachroo et al. 2001 Proc Natl Acad Sci USA 98:9448-9453), mpk4, in a MAP kinase gene (Petersen et al. 2000, Cell 103:1111-20), and pmr4 (Vogel and Somerville 2000 Proc Natl Acad Sci USA 97:1897-1902). The recessive mutations cpr5 and cpr1 also confer resistance to *P. syringae* and cause a dwarf phenotype (Bowling et al 1997 Plant Cell 9:1573-1584; Bowling et al, 1994 Plant Cell 6:1845-1857).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., Science (1992) 258: 1350-1353; Weigel et al., Plant Physiology (2000) 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., Plant Cell (1996) 8:659-671, Schaffer et al., Cell (1998) 93: 1219-1229; Fridborg et al., Plant Cell (1999) 11: 1019-1032; Kardailsky et al., Science (1999) 286:1962-1965); Christensen S et al., $9^{th}$ International Conference on *Arabidopsis* Research. Univ. of Wisconsin-Madison, Jun. 24-28, 1998. Abstract 165). In one example, activation tagging was used to identify mutants with altered disease resistance (Weigel et al., supra).

SUMMARY OF THE INVENTION

The invention provides a transgenic plant comprising a plant transformation vector comprising a nucleotide sequence that encodes or is complementary to a sequence that encodes a PPR2 polypeptide or an ortholog thereof. The transgenic plant is characterized by having increased resistance to pathogens.

The present invention further provides a method of producing an altered pathogen resistance phenotype in a plant. The method comprises introducing into plant progenitor cells a vector comprising a nucleotide sequence that encodes or is complementary to a sequence encoding a PPR2 polypeptide or an ortholog thereof and growing a transgenic plant that expresses the nucleotide sequence. In one embodiment, the PPR2 polypeptide has at least 50% sequence identity to the amino acid sequence presented in SEQ ID NO:2 and comprises a SANT domain. In other embodiments, the PPR2 polypeptide has at least 80% or 90% sequence identity to or has the amino acid sequence presented in SEQ ID NO:2.

The invention further provides plants and plant parts obtained by the methods described herein.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., Molecular Cloning: A Laboratory Manual (Second Edition), Cold Spring Harbor Press, Plainview, N.Y., 1989, and Ausubel F M et al., Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein, the term "vector" refers to a nucleic acid construct designed for transfer between different host cells.

An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality.

An "altered pathogen resistance phenotype" refers to detectable change in the response of a genetically modified plant to pathogenic infection, compared to the similar, but non-modified plant. The phenotype may be apparent in the plant itself (e.g., in growth, viability or particular tissue morphology of the plant) or may be apparent in the ability of the pathogen to proliferate on and/or infect the plant. As used herein, "improved pathogen resistance" refers to increased resistance to a pathogen.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes reference to a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Improved Pathogen Resistance Phenotype

We used an *Arabidopsis* activation tagging screen to identify the association between the gene we have designated "PPR2 (for *P. parasitica* Resistant)," predicted to encode a myb-related protein, and an altered pathogen resistance phenotype, specifically, increased resistance to the fungal pathogen *P. parasitica* (downy mildew). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al, supra). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 18 T2 seed were planted, grown to seedlings, and inoculated with *P. parasitica* spores. Disease symptoms on individual plants were scored based on the number of conidiophores that emerged. Accordingly, plants on which growth of conidiophores was reduced were identified as pathogen resistant.

An *Arabidopsis* line that showed increased resistance to *P. parasitica* infection was identified. The association of the PPR2 gene with the pathogen resistance phenotype was discovered by analysis of the genomic DNA sequence flanking the T-DNA insertion in the identified line. Accordingly, PPR2 genes and/or polypeptides may be employed in the development of genetically modified plants having a modified pathogen resistance phenotype. PPR2 genes may be used in the generation of crops and/or other plant species that have improved resistance to infection by *P. parasitica* and other oomycetes and may also be useful the generation of plant with improved resistance to fungal, bacterial, and/or other pathogens. Mis-expression of PPR2 genes may thus reduce the need for fungicides and/or pesticides. The modified pathogen resistance phenotype may further enhance the overall health of the plant.

PPR2 Nucleic Acids and Polypeptides

*Arabidopsis* PPR2 nucleic acid (coding) sequence is provided in SEQ ID NO:1 and in Genbank entry GI 12331602, nucleotides 20955-21335 (designated F22H5.3 and At1g75250). The corresponding protein sequence is provided in SEQ ID NO:2 and in GI 10092271.

As used herein, the term "PPR2 polypeptide" refers to a full-length PPR2 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active PPR2 polypeptide causes an altered pathogen resistance phenotype when mis-expressed in a plant. In a further preferred embodiment, mis-expression of the functionally active PPR2 polypeptide causes increased resistance to *P. parasitica* and/or other oomycetes. In another embodiment, a functionally active PPR2 polypeptide is capable of rescuing defective (including deficient) endogenous PPR2 activity when expressed in a plant or in plant cells; the rescuing polypeptide may be from the same or from a different species as that with defective activity. In another embodiment, a functionally active fragment of a full length PPR2 polypeptide (i.e., a native polypeptide having the sequence of SEQ ID NO:2 or a naturally occurring ortholog thereof) retains one of more of the biological properties associated with the full-length PPR2 polypeptide, such as signaling activity, binding activity, catalytic activity, or cellular or extra-cellular localizing activity. Some preferred PPR2 polypeptides display DNA binding activity. A PPR2 fragment preferably comprises a PPR2 domain, such as a C- or N-terminal or catalytic domain, among others, and preferably comprises at least 10, preferably at least 20, more preferably at least 25, and most preferably at least 50 contiguous amino acids of a PPR2 protein. Functional domains can be identified using the PFAM program (Bateman A et al., 1999 Nucleic Acids Res 27:260-262; website at pfam.wustl.edu). A preferred PPR2 fragment comprises a SANT domain (SM00395) identified by PFAM, at approximately amino acids 8-60. Functionally active variants of full-length PPR2 polypeptides or fragments thereof include polypeptides with amino acid insertions, deletions, or substitutions that retain one of more of the biological properties associated with the full-length PPR2 polypeptide. In some cases, variants are generated that change the post-translational processing of a PPR2 polypeptide. For instance, variants may have altered protein transport or protein localization characteristics or altered protein half-life compared to the native polypeptide.

As used herein, the term "PPR2 nucleic acid" encompasses nucleic acids with the sequence provided in or complementary to the sequence provided in SEQ ID NO:1, as well as functionally active fragments, derivatives, or orthologs thereof. A PPR2 nucleic acid of this invention may be DNA, derived from genomic DNA or cDNA, or RNA.

In one embodiment, a functionally active PPR2 nucleic acid encodes or is complementary to a nucleic acid that encodes a functionally active PPR2 polypeptide. Included within this definition is genomic DNA that serves as a template for a primary RNA transcript (i.e., an mRNA precursor) that requires processing, such as splicing, before encoding the functionally active PPR2 polypeptide. A PPR2 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed PPR2 polypeptide, or an intermediate form. A PPR2 polynucleotide can also include heterologous coding sequences, for example, sequences that encode a marker included to facilitate the purification of the fused polypeptide, or a transformation marker.

In another embodiment, a functionally active PPR2 nucleic acid is capable of being used in the generation of loss-of-function pathogen resistance phenotypes, for instance, via antisense suppression, co-suppression, etc.

In one preferred embodiment, a PPR2 nucleic acid used in the methods of this invention comprises a nucleic acid sequence that encodes or is complementary to a sequence that encodes a PPR2 polypeptide having at least 50%, 60%, 70%, 75%, 80%, 85%, 90%, 95% or more sequence identity to the polypeptide sequence presented in SEQ ID NO:2.

In another embodiment a PPR2 polypeptide of the invention comprises a polypeptide sequence with at least 50% or 60% identity to the PPR2 polypeptide sequence of SEQ ID NO:2, and may have at least 70%, 80%, 85%, 90% or 95% or more sequence identity to the PPR2 polypeptide sequence of SEQ ID NO:2. In another embodiment, a PPR2 polypeptide comprises a polypeptide sequence with at least 50%, 60%, 70%, 80%, 85%, 90% or 95% or more sequence identity to a functionally active fragment of the polypeptide presented in SEQ ID NO:2, such as a SANT domain. In yet another embodiment, a PPR2 polypeptide comprises a polypeptide sequence with at least 50%, 60%, 70%, 80%, or 90% identity to the polypeptide sequence of SEQ ID NO:2 over its entire length and comprises a SANT domain.

In another aspect, a PPR2 polynucleotide sequence is at least 50% to 60% identical over its entire length to the PPR2 nucleic acid sequence presented as SEQ ID NO:1, or nucleic acid sequences that are complementary to such a PPR2 sequence, and may comprise at least 70%, 80%, 85%, 90% or 95% or more sequence identity to the PPR2 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., supra). In some embodiments, a nucleic acid molecule of the invention is capable of hybridizing to a nucleic acid molecule containing the nucleotide sequence of SEQ ID NO:1 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate). In other embodiments, moderately stringent hybridization conditions are used that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a PPR2 polypeptide can be produced. For example, codons may be selected to increase the rate at which expression of the polypeptide occurs in a particular host species, in accordance with the optimum codon usage dictated by the particular host organism (see, e.g., Nakamura Y et al, Nucleic Acids Res (1999) 27:292). Such sequence variants may be used in the methods of this invention.

The methods of the invention may use orthologs of the *Arabidopsis* PPR2. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach and Dveksler (Eds.) PCR Primer: A Laboratory Manual, Cold Spring Harbor Laboratory Press, NY, 1989). For instance, methods for generating a cDNA library from the plant species of interest and probing the library with partially homologous gene probes are described in Sambrook et al. A highly conserved portion of the *Arabidopsis* PPR2 coding sequence may be used as a probe. PPR2 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known PPR2 polypeptides are used for ortholog isolation. Western blot analysis can determine that a PPR2 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., supra. Once the candidate ortholog(s) are identified by any of these means, candidate orthologous sequence are used as bait (the "query") for the reverse BLAST against sequences from *Arabidopsis* or other species in which PPR2 nucleic acid and/or polypeptide sequences have been identified.

PPR2 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., Methods Enzymol. (1991) 204:125-39), may be used to introduce desired changes into a cloned nucleic acid.

In general, the methods of the invention involve incorporating the desired form of the PPR2 nucleic acid into a plant expression vector for transformation of in plant cells, and the PPR2 polypeptide is expressed in the host plant.

An isolated PPR2 nucleic acid molecule is other than in the form or setting in which it is found in nature and is identified and separated from least one contaminant nucleic acid molecule with which it is ordinarily associated in the natural source of the PPR2 nucleic acid. However, an isolated PPR2 nucleic acid molecule includes PPR2 nucleic acid molecules contained in cells that ordinarily express PPR2 where, for example, the nucleic acid molecule is in a chromosomal location different from that of natural cells.

Generation of Genetically Modified Plants with a Pathogen Resistance Phenotype

PPR2 nucleic acids and polypeptides may be used in the generation of genetically modified plants having a modified pathogen resistance phenotype; in general, improved resistance phenotypes are of interest. Pathogenic infection may affect seeds, fruits, blossoms, foliage, stems, tubers, roots, etc. Accordingly, resistance may be observed in any part of the plant. In a preferred embodiment, altered expression of the PPR2 gene in a plant is used to generate plants with increased resistance to *P. parasitica*. In a further preferred embodiment, plants that mis-express PPR2 may also display altered resistance to other pathogens. Other oomycete pathogens of interest include *Pythium* spp, *Phytophthora* spp, *Bremia lactucae*, *Peronosclerospora* spp., *Pseudoperonospora*. *Sclerophthora macrospora*, *Sclerospora graminicola*, *Plasmopara viticola*, and *Albugo candidia*. Fungal pathogens of interest include *Alternaria brassicicola*, *Botrytis cinerea*, *Erysiphe cichoracearum*, *Fusarium oxysporum*, *Plasmodiophora brassica*, *Rhizoctonia solani*, *Colletotrichum coccode*, *Sclerotinia* spp., *Aspergillus* spp., *Penicillium* spp., *Ustilago* spp., and *Tilletia* spp. Bacterial pathogens of interest include *Agrobacterium tumefaciens*, *Erwinia tracheiphila*, *Erwinia stewartii*, *Xanthomonas phaseoli*, *Erwinia amylovora*, *Erwinia carotovora*, *Pseudomonas syringae*, *Pelargonium* spp, *Pseudomonas cihorii*, *Xanthomonas fragariae*, *Pseudomonas morsprunorum*, *Xanthomonas campestris*.

The methods described herein are generally applicable to all plants. Although activation tagging and gene identification is carried out in *Arabidopsis*, the PPR2 gene (or an ortholog, variant or fragment thereof) may be expressed in any type of plant. In preferred embodiments, the invention is directed to crops including maize, soybean, cotton, rice, wheat, barley, tomato, canola, turfgrass, and flax. Other crops include alfalfa, tobacco, and other forage crops. The invention may also be directed to fruit- and vegetable-bearing plants, plants used in the cut flower industry, grain-producing plants, oil-producing plants, and nut-producing plants, among others.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a PPR2 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature.

Expression (including transcription and translation) of PPR2 may be regulated with respect to the level of expression, the tissue type(s) where expression takes place and/or developmental stage of expression. A number of heterologous regulatory sequences (e.g., promoters and enhancers) are available for controlling the expression of a PPR2 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, Transgenic Res (1992) 1:285-297), the CsVMV promoter (Verdaguer B et al., Plant Mol Biol (1998) 37:1055-1067) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., Plant Mol Bio (1993) 21:625-640). In one preferred embodiment, PPR2 expression is under the control of a pathogen-inducible promoter (Rushton et al., The Plant Cell (2002) 14:749-762).

In one preferred embodiment, PPR2 expression is under control of regulatory sequences from genes whose expression is associated with the CsVMV promoter.

In yet another aspect, in some cases it may be desirable to inhibit the expression of endogenous PPR2 in a host cell. Exemplary methods for practicing this aspect of the invention include, but are not limited to antisense suppression (Smith, et al., Nature (1988) 334:724-726; van der Krol et al., Biotechniques (1988) 6:958-976); co-suppression (Napoli, et al., Plant Cell (1990) 2:279-289); ribozymes (PCT Publication WO 97/10328); and combinations of sense and antisense (Waterhouse, et al., Proc. Natl. Acad. Sci. USA (1998) 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc. Natl. Acad. Sci. USA (1988) 85:8805-8809), a partial cDNA sequence including fragments of 5' coding sequence, (Cannon et al., Plant Molec. Biol. (1990) 15:39-47), or 3' non-coding sequences (Ch'ng et al., Proc. Natl. Acad. Sci. USA (1989) 86:10006-10010). Cosuppression techniques may use the entire cDNA sequence (Napoli et al., supra; van der Krol et al., The Plant Cell (1990) 2:291-299), or a partial cDNA sequence (Smith et al., Mol. Gen. Genetics (1990) 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, (1999) Arch Virol Suppl 15:189-201]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., Cur Opin Plant Biol. (1999) 2(2):96-103; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with a Pathogen Resistance Phenotype

The invention further provides a method of identifying plants that have mutations in endogenous PPR2 that confer increased pathogen resistance, and generating pathogen-resistant progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. PPR2-specific PCR are used to identify whether a mutated plant has a PPR2 mutation. Plants having PPR2 mutations may then be tested for pathogen resistance, or alternatively, plants may be tested for pathogen resistance, and then PPR2-specific PCR is used to determine whether a plant having increased pathogen resistance has a mutated PPR2 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the PPR2 gene or orthologs of PPR2 that may confer increased resistance to pathogens (see Foolad et al., Theor Appl Genet. (2002) 104(6-7):945-958; Rothan et al., Theor Appl Genet (2002) 105(1):145-159); Dekkers and Hospital, Nat Rev Genet. (2002) Jan;3(1):22-32). Thus, in a further aspect of the invention, a PPR2 nucleic acid is used to identify whether a plant having increased pathogen resistance has a mutation in endogenous PPR2 or has a particular allele that causes the increased pathogen resistance.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a PPR2 Phenotype by Transformation with an Activation Tagging Construct Mutants were generated using the activation tagging "ACT-TAG" vector, pSKI015 (GI 6537289; Weigel D et al., 2000). Standard methods were used for the generation of Arabidop-

*sis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed was collected from T1 plants and stored in an indexed collection, and a portion of the T2 seed was accessed for the screen.

Approximately 18 T2 seeds from each of the greater than 40,00 lines tested were planted in soil. The seed were stratified for three days and then grown in the greenhouse for seven days. The seedlings were inoculated with approximately $1 \times 10^5$ conidia per ml *P. parasitica* spores and incubated in a dew room at 18° C. and 100% humidity for 24 hours. The plants were then moved to a growth room at 20° C. and 60% relative humidity with ten-hour long light period for six days. Individual plants were evaluated for the presence or absence of conidiophores on cotyledons. Lines in which at least a single plant showed no conidiophore growth were re-tested in a secondary screen by releasing three sets of 18 seed and screening for resistance to *P. parasitica* growth as before.

Lines in which a significant number of plants showed no conidiophores after infection were subjected to a tertiary screen. Approximately 54 T2 seed were released, planted individually and infected with *P. parasitica* as before. The plants were evaluated for the number of conidiophores growing on a single cotyledon and ranked by the following scoring system: a score of 0 indicates 0 conidiophores per cotyledon, 1 indicates 1-5 conidiophores per cotyledon, 2 indicates 6-10 conidiophores per cotyledon, 3 indicates 11-20 conidiophores per cotyledon, and 4 indicates greater than 20 conidiophores per cotyledon The ACTTAG line designated W000058335 was identified as having an increased resistance phenotype. Specifically, 15.2% of individual plants showed no conidiophores in the secondary screen. In the tertiary screen, 31 plants scored as 0 (39.2%), 31 as 1 (39.2%), 4 as 2 (5.1%), 10 as 3 (12.7%) and 3 as 4 (3.8%). Control wild-type Col-0 plants were more susceptible; 36 plants scored 0 (7.6%), 21 as 1 (4.4%), 79 as 2 (16.6%), 250 as 3 (52.5%) and 90 as 4 (18.9%).

Example 2

Characterization of the T-DNA Insertion in Plants Exhibiting the Altered Pathogen Resistance Phenotype.

We performed standard molecular analyses, essentially as described in patent application PCT WO0183697, to determine the site of the T-DNA insertion associated with the increased pathogen resistance phenotype. Briefly, genomic DNA was extracted from plants exhibiting increased pathogen resistance. PCR, using primers specific to the pSKI015 vector, confirmed the presence of the 35S enhancer in plants from line W000058335, and Southern blot analysis verified the genomic integration of the ACTTAG T-DNA and showed the presence of a single T-DNA insertion in the transgenic line.

Plasmid rescue and inverse PCR were used to recover genomic DNA flanking the T-DNA insertion, which was then subjected to sequence analysis.

The sequence flanking the right T-DNA border was subjected to a basic BLASTN search and/or a search of the *Arabidopsis* Information Resource (TAIR) database (available at the arabidopsis.org website), which revealed sequence identity to BAC F22H5, (GI 12331602), mapped to chromosome 1. The junction of the left border of the T-DNA is at nt 20167 of F22H5, and the right border junction is at nt 20229. Sequence analysis revealed that the T-DNA had inserted in the vicinity (i.e., within about 10 kb) of the gene whose nucleotide sequence is presented as SEQ ID NO: 1 and GI 12331602, nucleotides 20955-21335, and which we designated PPR2. Specifically, the right border was approximately 500 bp upstream of the start codon of SEQ ID NO:1.

Example 3

Analysis of *Arabidopsis* PPR2 Sequence

The amino acid sequence predicted from the PPR2 nucleic acid sequence is presented in SEQ ID NO:2 and GI 10092271.

Sequence analyses were performed with BLAST (Altschul et al., 1997, J. Mol. Biol. 215:403-410), PFAM (Bateman et al., 1999), PSORT (Nakai K, and Horton P, 1999,Trends Biochem Sci 24:34-6), and CLUSTALW (Thompson J D et al, 1994, Nucleic Acids Res 22:4673-4680), among others.

The PPR2 protein has been characterized as a myb-related protein. PFAM analysis indicated a SANT DNA-binding domain at approximately amino acids 8-60.

The retroviral oncogene v-myb, and its cellular counterpart c-myb, encode nuclear DNA-binding proteins (Klempnauer and Sippel, 1987, EMBO J. 6: 2719-2725; Biednkapp et al. 1988, Nature 335: 835-837). These belong to the SANT domain family that specifically recognize the sequence YAAC(G/T)G (Aasland et al. 1996, Trends Biochem. Sci. 21:87-88). In myb, one of the most conserved regions consisting of three tandem repeats has been shown to be involved in DNA-binding.

Analysis using BLASTP or TBLASTN identified a number of related proteins and proteins predicted from nucleic acid (generally EST) sequences in other plant species. Related sequences, which are candidate orthologs, are presented in SEQ ID NOs 3-14 and descriptions from GenBank are provided below:

SEQ ID NO:3 translation, gi|887283|gb|L38243.1|L38243 BNAF0581E Mustard flower buds *Brassica rapa* cDNA—ORF 98aa *Brassica rapa*

SEQ ID NO:4 translation, gi|18459015|gb|BM437293.1|BM437293 VVA017C08__ 54081 An expressed sequence tag database for abiotic st 75aa *Vitis vinifera*

SEQ ID NO:5 translation, gi|15288211|gb|BI472102.1|BI472102 sah99e03.y1 Gm-c1050 Glycine max cDNA clone GENOME SYSTEMS CLONE 97aa Glycine max SEQ ID NO:6 translation, gi|15258392|gb|BI433702.1|BI433702 EST536463 *P. infestans*-challenged leaf *Solanum tuberosum* cDNA clo 88aa *Solanum tuberosum*

SEQ ID NO: translation, gi|14492357|gb|BI071737.1|BI071737 C063P09U *Populus* strain T89 leaves *Populus tremula×Populus trem* 71aa P o SEQ ID NO:8 translation, gi|7981380|emb|CAB91874.1| (AJ277944) myb-related protein [*Lycopersicon esculentum*] 88aa *Lycopersicon esculentum*

SEQ ID NO:9 gi|5091605|gb|AAD39594.1|AC007858__8 (AC007858) 10A19I.9 [*Oryza sativa*] 126aa *Oryza sativa*

SEQ ID NO:10 gi|5091604|gb|AAD39593.1|AC007858__7 (AC007858) 10A19I.8 [*Oryza sativa*] 236aa *Oryza sativa*

SEQ ID NO:11 gi|18394750|ref|NP__564087.1| (NM__ 101808) myb-related protein, putative [*Arabidopsis thaliana*] 92aa *Arabidopsis thaliana*

SEQ ID NO:12 gi|15226604|ref|NP_179759.1| (NM_127736) unknown protein [*Arabidopsis thaliana*].gi|4567225|gb|AAD236 101aa *Arabidopsis thaliana*

SEQ ID NO:13 gi|15234999|ref|NP_195636.1| (NM_120086) putative protein [*Arabidopsis thaliana*].gi|7487341|pir||T08 97aa *Arabidopsis thaliana*

SEQ ID NO:14 gi|8778436|gb|AAF79444.1|AC025808_26 F18O14.26 [*Arabidopsis thaliana*]

Example 4

Confirmation of Phenotype Genotype Association

PCR analysis, using primers to sequences in pSKI015 or flanking the insert, was used to detect lines containing or lacking the insert. W000058335 individuals analyzed in the tertiary screen were genotyped. Results indicated that plants that were homozygous or hemizygous for the insert were more resistant to *P. parasitica* infection than plants that were homozygous wild-type; 100% of the plants homozygous for the insert and 97% of the plants hemizygous for the insertion received resistance scores of 0 or 1 while only 31% of the wild-type segregants scored 0 or 1. These results suggest that the *P. parasitica* resistance trait in W000058335 is caused by the overexpression of PPR2 and is inherited in a dominant manner RT-PCR analysis showed that the PPR2 gene was overexpressed in plants from the line displaying the *P. parasitica* resistance phenotype. Specifically, RNA was extracted from tissues derived from plants exhibiting the resistance phenotype and from wild type COL-0 plants. RT-PCR was performed using primers specific to the sequence presented as SEQ ID NO:1, to other predicted genes in the vicinity of the T-DNA insertion (At1g75240, At1g75260, and At1g75270), and to a constitutively expressed actin (positive control). The results showed that plants displaying the PPR2 phenotype over-expressed the mRNA for the PPR2 gene, indicating the enhanced expression of the PPR2 gene is correlated with the PPR2 phenotype.

Example 5

Recapitulation of Pathogen Resistance Phenotype

*Arabidopsis* plants of the Ws ecotype are transformed by agrobacterium mediated transformation with a construct containing the coding sequences of the PPR2 gene (At1g75250, alias F22H5.3; GI:10092271) behind the CsVMV promoter and in front of the nos terminator or a control gene unrelated to pathogen resistance. Both of these constructs contain the nptII gene to confer kanamycin resistance in plants. T1 seed is harvested from the transformed plants and transformants selected by germinating seed on agar medium containing kanamycin. Kanamycin resistant transformants are transplanted to soil after 7 days and grown for 4 weeks. Control plants are germinated on agar medium without kanamycin, transplanted to soil after 7 days and grown in soil for 4 weeks To evaluate pathogen resistance, transformants and control plants are sprayed with a suspension of $1 \times 10^5$ conidia per ml of *P. parasitica*, incubated at 100% humidity for 1 day, and grown for 6 more days in the growth room After this growth period, plants are rated for severity of disease symptoms. A score of 0 means the leaves have 0-10% of the number of conidiophores growing on the leaf surface as a fully susceptible plant, 1 means 10-25% the number of conidiophores, 2 means 25-50%, 3 means 50-75% and 4 means 75-100%. Plants transformed with PPR2, and plants transformed with the control gene are examined.

Degree-of-infection scores are obtained from each plant tested. As a group, the PPR2 transformants are more resistant to *P. parasitica* infection than control plants demonstrating that plants over-expressing PPR2 are significantly more resistant to *P. parasitica* infection than wild-type plants.

It is claimed:

1. A method of producing a plant having increased pathogen resistance, said method comprising:
   a) introducing into cells of the plant a plant transformation vector comprising a nucleotide sequence that encodes a Myb polypeptide that confers *Peronospora parasitica* resistance (PPR2), said Myb polypeptide selected from the group consisting of: a polypeptide having at least 95% sequence identity to SEQ ID NO: 11; and an *Arabidopsis thaliana* polypeptide having at least 95% sequence identity to SEQ ID NO: 11, and b) growing the transformed cells to produce a transgenic plant, wherein said nucleotide sequence is expressed, and said transgenic plant exhibits increased pathogen resistance relative to a control plant.

2. A transformed plant obtained by the method of claim 1.

3. A transformed plant part obtained from the plant according to claim 2.

4. The transformed plant of claim 2, wherein the nucleotide sequence encodes an *Arabidopsis thaliana* polypeptide having at least 95% sequence identity to SEQ ID NO: 11.

5. The method of claim 1, wherein the *Arabidopsis thaliana* polypeptide has a sequence having at least 95% sequence identity to SEQ ID NO: 11.

* * * * *

UNITED STATES PATENT AND TRADEMARK OFFICE
CERTIFICATE OF CORRECTION

PATENT NO. : 7,829,759 B2
APPLICATION NO. : 12/400577
DATED : November 9, 2010
INVENTOR(S) : Federspiel et al.

It is certified that error appears in the above-identified patent and that said Letters Patent is hereby corrected as shown below:

On the Title Page Item (56) OTHER PUBLICATIONS:

Page 2, right column, "would-" should read --wound- --.

Page 2, right column, "bacteria*Arabidopsis*" should read --bacteria *Arabidopsis*--.

Column 2, line 22, "1965);" should read --1965;--.

Column 4, line 3, "progagules" should read --propagules--.

Column 5, line 38, "useful the" should read --useful in the--.

Column 5, line 55, "or" should read --of--.

Column 6, line 3, "of" should read --or--.

Column 6, line 20, "of" should read --or--.

Column 9, line 25, "sequence" should read --sequences--.

Column 9, line 34, "sequence" should read --sequences--.

Column 9, line 40, "of in" should read --in--.

Column 9, line 44, "from least" should read --from at least--.

Column 9, line 66, "*Pseudoperonospora.*" should read --*Pseudoperonospora spp*,--.

Column 10, line 10, "*cihorii*," should read --*cichorii*,--.

Column 10, line 34, "bombardment" should read --bombardment,--.

Column 12, line 42, "159);" should read --159;--.

Column 13, line 22, "18 seed" should read --18 seeds--.

Column 13, line 34, "cotyledon" should read --cotyledon.--.

Column 14, line 53, "NO:" should read --NO:7--.

Column 15, line 13, "Phenotype Genotype" should read --Phenotype/Genotype--.

Column 15, line 21, "insertion" should read --insert--.

Signed and Sealed this
Fourteenth Day of June, 2011

David J. Kappos
*Director of the United States Patent and Trademark Office*

CERTIFICATE OF CORRECTION (continued)
U.S. Pat. No. 7,829,759 B2

Column 15, line 26, "manner" should read --manner.--.

Column 16, line 21, "4 weeks" should read --4 weeks.--.

Column 16, line 24, "room" should read --room.--.

SEQUENCE LISTING

```
<160> NUMBER OF SEQ ID NOS: 14

<210> SEQ ID NO 1
<211> LENGTH: 381
<212> TYPE: DNA
<213> ORGANISM: Arabidopsis thaliana

<400> SEQUENCE: 1
atggcgtcaa actcaagaag ttcaatctca ccatggacgt ttagtcaaaa caagatgttc      60
gagagggcct tggcagttta cgacaaggac acacccgacc gatggcacaa tgtggcaaaa     120
gctgtcggag ggaaaactgt agaagaagtg aagcgccact atgacattct cgtcgaggat     180
ctcatcaaca tcgagactgg tcgtgtccct ttgcccaatt acaagacctt cgaatctaac     240
tcaagaagca tcaatgactt tgacacaagg tatataacta aatatctata tatgatgctc     300
tcgatatatt ttgataatca ttctagtgat tttgagaaat tctctcaaaa agttcttgta     360
agttatattt ctttggttta a                                               381

<210> SEQ ID NO 2
<211> LENGTH: 126
<212> TYPE: PRT
<213> ORGANISM: Arabidopsis thaliana

<400> SEQUENCE: 2
```

```
Met Ala Ser Asn Ser Arg Ser Ser Ile Ser Pro Trp Thr Phe Ser Gln
1               5                   10                  15

Asn Lys Met Phe Glu Arg Ala Leu Ala Val Tyr Asp Lys Asp Thr Pro
            20                  25                  30

Asp Arg Trp His Asn Val Ala Lys Ala Val Gly Gly Lys Thr Val Glu
        35                  40                  45

Glu Val Lys Arg His Tyr Asp Ile Leu Val Glu Asp Leu Ile Asn Ile
    50                  55                  60

Glu Thr Gly Arg Val Pro Leu Pro Asn Tyr Lys Thr Phe Glu Ser Asn
65                  70                  75                  80

Ser Arg Ser Ile Asn Asp Phe Asp Thr Arg Tyr Ile Thr Lys Tyr Leu
            85                  90                  95

Tyr Met Met Leu Ser Ile Tyr Phe Asp Asn His Ser Ser Asp Phe Glu
            100                 105                 110

Lys Phe Ser Gln Lys Val Leu Val Ser Tyr Ile Ser Leu Val
            115                 120                 125
```

```
<210> SEQ ID NO 3
<211> LENGTH: 98
<212> TYPE: PRT
<213> ORGANISM: Brassica rapa

<400> SEQUENCE: 3
```

```
Met Ala Ser Ser Met Ser Ser Ser Trp Thr Ser Lys Gln Asn Lys
1               5                   10                  15

Ile Phe Glu Arg Ala Leu Ala Val Tyr Asp Lys Asp Thr Pro Asp Arg
            20                  25                  30

Trp Gln Asn Val Ala Lys Ala Val Gly Asn Lys Ser Ala Glu Glu Val
        35                  40                  45

Lys Arg His Tyr Asp Ile Leu Val Glu Asp Leu Met Asn Ile Glu Gln
    50                  55                  60

Asp Leu Val Pro Leu Pro Lys Tyr Lys Thr Val Asp Val Gly Asn Lys
65                  70                  75                  80

Ser Arg Gly Ile Asn Gly Tyr Gly Leu Arg Leu Met Lys Asn Ile Glu
            85                  90                  95

Val Gln
```

```
<210> SEQ ID NO 4
<211> LENGTH: 75
<212> TYPE: PRT
<213> ORGANISM: Vitis vinifera

<400> SEQUENCE: 4
```

```
Met Ala Ser Thr Ser Leu Lys Ser Ser Gly Ser Trp Thr Pro Lys Gln
1               5                   10                  15

Asn Lys Leu Phe Glu Lys Ala Leu Ala Leu Tyr Asp Arg Asp Thr Pro
            20                  25                  30

Asp Arg Trp Gln Asn Val Ala Asn Ala Val Gly Gly Lys Ser Ala Glu
        35                  40                  45

Glu Val Lys Gln His Tyr Glu Ile Leu Ile Arg Asp Leu Lys His Ile
    50                  55                  60

Glu Ser Gly Arg Val Pro Ile Pro Asn Tyr Lys
65                  70                  75
```

```
<210> SEQ ID NO 5
<211> LENGTH: 97
```

```
<212> TYPE: PRT
<213> ORGANISM: Glycine max

<400> SEQUENCE: 5

Met Glu Ser Cys Ser Ile Ser Ala Ser Gly Ser Trp Ser Val Lys Asp
1               5                   10                  15

Asn Lys Ala Phe Glu Lys Ala Leu Ala Val Tyr Asp Lys Asp Thr Pro
            20                  25                  30

Asp Arg Trp Tyr Asn Val Ala His Ala Val Gly Gly Lys Thr Pro Glu
        35                  40                  45

Glu Val Lys Arg His Tyr Glu Leu Leu Val Gln Asp Val Lys His Ile
50                  55                  60

Glu Ser Gly Arg Val Pro Phe Pro Asn Tyr Lys Lys Thr Thr Ser Glu
65                  70                  75                  80

Ser Thr Asp Gln Glu Glu Lys Arg Leu Arg Asn Leu Asn Leu Asn Leu
                85                  90                  95

Gln

<210> SEQ ID NO 6
<211> LENGTH: 88
<212> TYPE: PRT
<213> ORGANISM: Solanum tuberosum

<400> SEQUENCE: 6

Met Ala Ser Ser Ser Leu Gln Ser Ser Ser Trp Thr Pro Gln Gln Asn
1               5                   10                  15

Lys Leu Phe Glu Arg Ala Leu Ala Gln Phe Asp Lys Asp Thr Pro Asp
            20                  25                  30

Arg Trp Gln Asn Val Ala Arg Ala Val Gly Gly Gly Lys Ser Ala Asp
        35                  40                  45

Glu Val Lys Arg His Tyr Glu Ile Leu Ile Glu Asp Leu Lys Arg Ile
50                  55                  60

Glu Ser Gly Arg Val Pro Leu Pro Thr Tyr Thr His Glu Gln Gln Arg
65                  70                  75                  80

Leu Leu Arg Tyr Met Asn Leu His
                85

<210> SEQ ID NO 7
<211> LENGTH: 71
<212> TYPE: PRT
<213> ORGANISM: Populus tremula

<400> SEQUENCE: 7

Met Ser Ser Ser His Gln Thr Pro Arg Asn Ser Ser Ser Trp Thr
1               5                   10                  15

Pro Arg Glu Asn Lys Leu Phe Glu Lys Ala Leu Ala Leu Phe Asp Lys
            20                  25                  30

Asp Thr Pro Asp Arg Trp Lys Asn Val Ala Lys Ala Val Gly Gly Val
        35                  40                  45

Lys Ser Ala Glu Glu Val Lys Arg His Tyr Glu Ile Leu Ile Glu Asp
50                  55                  60

Leu Lys His Ile Glu Pro Ala
65                  70

<210> SEQ ID NO 8
<211> LENGTH: 88
<212> TYPE: PRT
<213> ORGANISM: Lycopersicon esculentum
```

```
<400> SEQUENCE: 8

Met Ser Ser Met Ser Ser Gln His Gly Ser Ser Gly Ser Trp Thr Ala
1               5                   10                  15

Lys Gln Asn Lys Ala Phe Glu Lys Ala Leu Ala Val Tyr Asp Lys Glu
            20                  25                  30

Thr Arg Asp Arg Trp Ser Asn Val Ala Lys Ala Val Gly Gly Lys Thr
        35                  40                  45

Ala Glu Glu Val Lys Arg His Tyr Glu Ile Leu Leu Arg Asp Val Phe
    50                  55                  60

Phe Ile Asp Asn Gly Met Val Pro Phe Pro Lys Tyr Lys Thr Thr Gly
65                  70                  75                  80

Gly Ser His Asn Ser Thr Ser Asp
                85

<210> SEQ ID NO 9
<211> LENGTH: 126
<212> TYPE: PRT
<213> ORGANISM: Oryza sativa

<400> SEQUENCE: 9

Met Ala Ser Ala Ala Gly Ser Lys Gln Gln Ala Met Met Ser Leu
1               5                   10                  15

Pro Ser Ser Arg Gly Gly Gly Gly Gly Trp Thr Gln Arg Gln Asn
            20                  25                  30

Lys Gln Phe Glu Cys Ala Leu Ala Val Tyr Asp Lys Glu Thr Pro Asp
            35                  40                  45

Arg Trp His Asn Ile Ala Arg Tyr Met Gly Gly Ala Lys Ser Ala Asp
        50                  55                  60

Glu Val Arg Arg His Phe Asp His Leu Val Glu Asp Val Ser Arg Ile
65                  70                  75                  80

Glu Ser Gly Arg Val Pro Phe Pro Arg Tyr Ser Ser Ser Ser Ser Ser
                85                  90                  95

Arg Gly Ala Asp Asp Gly Asn Arg Leu Leu Thr Val Phe His Leu Ser
            100                 105                 110

Ser Val Pro Arg Thr Arg Asn Ala Asn His Lys Phe Asn Thr
        115                 120                 125

<210> SEQ ID NO 10
<211> LENGTH: 236
<212> TYPE: PRT
<213> ORGANISM: Oryza sativa

<400> SEQUENCE: 10

Met Ala Gln Gln Ala Arg Ala Gln Trp Pro Gln Lys Gln Asn Lys Leu
1               5                   10                  15

Phe Glu Gln Ala Leu Ala Val Tyr Asp Lys Glu Thr Pro Asp Arg Trp
            20                  25                  30

His Asn Ile Ala Arg Ala Val Gly Gly Lys Ser Ala Glu Asp Val
            35                  40                  45

Lys Arg Tyr Tyr Glu Met Leu Glu Glu Asp Ile Lys His Ile Glu Ser
    50                  55                  60

Gly Lys Val Pro Phe Pro Ala Tyr Arg Cys Pro Ala Ala Gly Tyr
65                  70                  75                  80

Gln Ala Glu Ser Arg Pro Ser Thr Ala Ala Glu Pro Ser Arg Leu Pro
                85                  90                  95
```

```
Leu Ser Asp Ser Gly Leu Ser Gly Ile Arg Pro Thr Gln Tyr Pro Pro
            100                 105                 110

Asp Gly Glu Leu Ser Pro Pro Arg His Arg Leu Arg Arg Gly Asn
            115                 120                 125

Gln Pro Ile Pro Ser Tyr Lys Pro Ser Pro Ser Arg Glu Gly Ile Phe
            130                 135                 140

Tyr Trp Glu Val Val Ala Ala Leu Lys Ser Arg Gly Thr Gly Ala
145                 150                 155                 160

Thr Ser Thr Pro Trp Ile Arg Leu Leu Leu Pro Gly Leu Thr Val Cys
                    165                 170                 175

Arg Leu Leu Gly Ser Ser Gly Cys Phe Asp Ala Trp Met Leu Ser Thr
                180                 185                 190

Ala Arg Leu Met Val Val Asn Thr Tyr Trp Met Ser Tyr Leu Thr Arg
                195                 200                 205

Ser Pro Glu Phe His Leu Asn Phe Pro His Ile Asn Leu Arg Lys Tyr
            210                 215                 220

Glu Val Val Cys Val Gln Pro Gly Phe Met Gln Glu
225                 230                 235
```

<210> SEQ ID NO 11
<211> LENGTH: 92
<212> TYPE: PRT
<213> ORGANISM: Arabidopsis thaliana

<400> SEQUENCE: 11

```
Met Ala Ser Ser Ser Met Ser Ser Ser Ser Trp Thr Ser Lys Gln
1               5                   10                  15

Asn Lys Met Phe Glu Arg Ala Leu Ala Val Tyr Asp Lys Asp Thr Pro
                20                  25                  30

Asp Arg Trp Gln Asn Val Ala Lys Ala Val Gly Ser Lys Ser Ala Glu
            35                  40                  45

Glu Val Lys Arg His Tyr Asp Ile Leu Val Glu Asp Leu Met Asn Ile
        50                  55                  60

Glu Gln Asp Leu Val Pro Leu Pro Lys Tyr Lys Thr Val Asp Val Gly
65                  70                  75                  80

Ser Lys Ser Arg Gly Ile Asp Asp Phe Asp Leu Arg
                85                  90
```

<210> SEQ ID NO 12
<211> LENGTH: 101
<212> TYPE: PRT
<213> ORGANISM: Arabidopsis thaliana

<400> SEQUENCE: 12

```
Met Ala Ser Gly Ser Met Ser Ser Tyr Gly Ser Gly Ser Trp Thr Val
1               5                   10                  15

Lys Gln Asn Lys Ala Phe Glu Arg Ala Leu Ala Val Tyr Asp Gln Asp
                20                  25                  30

Thr Pro Asp Arg Trp His Asn Val Ala Arg Ala Val Gly Gly Lys Thr
            35                  40                  45

Pro Glu Glu Ala Lys Arg Gln Tyr Asp Leu Leu Val Arg Asp Ile Glu
        50                  55                  60

Ser Ile Glu Asn Gly His Val Pro Phe Pro Asp Tyr Lys Thr Thr Thr
65                  70                  75                  80

Gly Asn Ser Asn Arg Gly Arg Leu Arg Asp Glu Glu Lys Arg Met Arg
                85                  90                  95
```

```
Ser Met Lys Leu Gln
            100

<210> SEQ ID NO 13
<211> LENGTH: 97
<212> TYPE: PRT
<213> ORGANISM: Arabidopsis thaliana

<400> SEQUENCE: 13

Met Ala Ser Ser Ser Met Ser Ser Gln Ser Gly Ser Trp Thr Ala
1               5                   10                  15

Lys Gln Asn Lys Ala Phe Glu Gln Ala Leu Ala Thr Tyr Asp Gln Asp
                20                  25                  30

Thr Pro Asn Arg Trp Gln Asn Val Ala Lys Val Val Gly Gly Lys Thr
            35                  40                  45

Thr Glu Glu Val Lys Arg His Tyr Glu Leu Leu Val Gln Asp Ile Asn
        50                  55                  60

Ser Ile Glu Asn Gly His Val Pro Phe Pro Asn Tyr Arg Thr Ser Gly
65                  70                  75                  80

Gly Cys Thr Asn Gly Arg Leu Ser Gln Glu Leu Lys Arg Tyr Val Leu
                85                  90                  95

Ser

<210> SEQ ID NO 14
<211> LENGTH: 639
<212> TYPE: PRT
<213> ORGANISM: Arabidopsis thaliana

<400> SEQUENCE: 14

Met Ala Ser Ser Ser Met Ser Ser Ser Ser Trp Thr Ser Lys Gln
1               5                   10                  15

Asn Lys Met Phe Glu Arg Ala Leu Ala Val Tyr Asp Lys Asp Thr Pro
                20                  25                  30

Asp Arg Trp Gln Asn Val Ala Lys Ala Val Gly Ser Lys Ser Ala Glu
            35                  40                  45

Glu Val Lys Arg His Tyr Asp Ile Leu Val Glu Asp Leu Met Asn Ile
        50                  55                  60

Glu Gln Asp Leu Val Asn Glu Tyr Glu Asn Pro Val Lys Leu Leu
65                  70                  75                  80

His Asp Val Lys Ile Ala Ile Cys Leu Arg Ile Gln Arg Asp Met Met
                85                  90                  95

Ala Lys Ile Ser Val Ala Val Leu Leu Ser Val Met Leu Leu Val Ser
                100                 105                 110

Ile Asn Ser Val Asp Ile Leu Ala Glu Glu Pro Thr Val Gly Gln
            115                 120                 125

Arg Val Asp Ser Ala Met Thr Ser Val Thr Asp Ala Phe Asn Glu His
        130                 135                 140

Gly Gly Pro Gln Ala Val Asp Thr Val Ser Ser Thr Phe Lys Ser Val
145                 150                 155                 160

Tyr Gly Trp Phe Gly Asp Lys Ala Lys Tyr Leu Glu Pro Ile Ser Ser
                165                 170                 175

Ser Cys Cys Ser Ser Ser Ser Ser Gly Glu Glu Asn Thr Ala
                180                 185                 190
```

```
Ala Ala Asn Met Thr Glu Met Glu Ala Ala Glu Ala Leu Ala Asp Leu
        195                 200                 205

Ala Gln Leu Ala Ile Met Arg Glu Gln Val Phe Glu Ser Ala Ala Ser
    210                 215                 220

Trp Gly Ser Lys Gly Lys Arg Val Arg Lys Val Lys Thr Glu Ser
225                 230                 235                 240

Pro Pro Ser Asp Ser Leu Leu Lys Pro Pro Asp Ser Asp Thr Leu Pro
                245                 250                 255

Thr Pro Asp Leu Ala Glu Glu Arg Leu Val Lys Glu Glu Glu Glu
            260                 265                 270

Glu Glu Val Glu Pro Ile Thr Lys Glu Leu Thr Lys Ala Pro Val Lys
        275                 280                 285

Ser Glu Ile Asn Gly Glu Thr Pro Lys Pro Ile Leu Ala Ser Thr Leu
    290                 295                 300

Ile Arg Cys Ser Arg Ser Asn Gly Cys Gly Arg Ser Arg Gln Asn Leu
305                 310                 315                 320

Ser Glu Ala Glu Arg Glu Glu Arg Arg Ile Arg Arg Ile Leu Ala Asn
                325                 330                 335

Arg Glu Ser Ala Arg Gln Thr Ile Arg Arg Arg Gln Ala Met Cys Glu
            340                 345                 350

Glu Leu Ser Lys Lys Ala Ala Asp Leu Thr Tyr Glu Asn Glu Asn Leu
        355                 360                 365

Arg Arg Glu Lys Asp Trp Ala Leu Lys Glu Phe Gln Ser Leu Glu Thr
    370                 375                 380

Ile Asn Lys His Leu Lys Glu Gln Val Leu Lys Ser Val Lys Pro Asp
385                 390                 395                 400

Thr Lys Glu Pro Glu Glu Ser Pro Lys Pro Ser Gln Val Glu Met Ser
                405                 410                 415

Thr Ser Ser Thr Pro Phe Tyr Phe Tyr Asn Gln Asn Pro Tyr Gln Leu
            420                 425                 430

Phe Cys Trp Pro His Val Thr Gln Ser Ser Asn Pro Met Ile Ser Pro
    435                 440                 445

Leu Glu Phe Pro Thr Ser Gly Gly Ala Ser Ala Lys Thr Ile Thr Thr
450                 455                 460

Gln Glu His Glu Asn Ala Ala Asp Asp Asn Gly Gln Lys Thr His Phe
465                 470                 475                 480

Tyr Val Val Pro Cys Pro Trp Phe Leu Pro Pro Asp His Ser Asn
                485                 490                 495

Gly Val Pro Phe Gly Leu Gln Asp Thr Gln Arg Gly Thr Phe Ser Asn
            500                 505                 510

Gly His His Ile Asp Asp Ser Ser Ala Arg Pro Met Asp Val Thr Glu
    515                 520                 525

Thr Pro Arg Ser His Leu Pro Thr Arg Ile Lys Glu Glu Asp Ser Gly
530                 535                 540

Ser Pro Glu Thr Arg Pro Leu Tyr Asp Leu Asn Glu Ser Ala Thr Glu
545                 550                 555                 560

Val Leu Ser Glu Gly Gly Asp Gly Phe Pro Val Thr Gln Gln Ala Tyr
                565                 570                 575

Ser Leu Lys His Glu Asp Val Ser Glu Thr Thr Asn Gly Val Thr Leu
            580                 585                 590
```

```
-continued

Met Pro Pro Gly His His Val Leu Ile Ser Leu Pro Glu Lys Lys His
        595                 600             605

Gly Ser Leu Ala Ala Ala Glu Ala Arg Lys Arg Arg Lys Glu Leu Thr
        610             615             620

Arg Leu Lys Asn Leu His Gly Arg Gln Cys Arg Met Gln Val Gly
625             630             635
```